United States Patent [19]

Rider

[11] 4,198,390

[45] Apr. 15, 1980

[54] SIMETHICONE ANTACID TABLET

[76] Inventor: Joseph A. Rider, 10 Charles Dean Rd., Mill Valley, Calif. 94941

[21] Appl. No.: 7,887

[22] Filed: Jan. 31, 1979

[51] Int. Cl.² ............... A61K 9/24; A61K 31/695; A61K 33/08; A61K 9/58

[52] U.S. Cl. ........................... 424/21; 424/14; 424/16; 424/32; 424/37; 424/156; 424/184

[58] Field of Search ............... 424/14, 16, 21, 32, 424/37, 154–158, 184

[56] References Cited

U.S. PATENT DOCUMENTS

| Re. 25,205 | 7/1962 | Fenistone | 424/32 |
|---|---|---|---|
| 462,990 | 11/1891 | Oppenheimer | 424/21 |
| 2,512,192 | 6/1950 | Yen et al. | 424/32 |
| 3,048,526 | 8/1962 | Boswell | 424/21 |
| 3,094,464 | 6/1963 | Joullie et al. | 424/35 |
| 3,096,248 | 7/1963 | Rudski | 424/35 |
| 3,382,150 | 5/1968 | Grass et al. | 424/156 |
| 3,501,571 | 3/1970 | Yen | 424/156 |
| 3,767,794 | 10/1973 | McVean et al. | 424/156 |
| 4,127,650 | 11/1978 | Buehler | 424/156 |
| 4,140,755 | 2/1979 | Sheth et al. | 424/21 |

Primary Examiner—Shep K. Rose
Attorney, Agent, or Firm—Merriam, Marshall & Bicknell

[57] ABSTRACT

A tablet containing at least two separate and discrete volume portions one of which contains simethicone and the other of which contains antacid. A barrier separates the two volume portions to maintain the simethicone out of contact with the antacid and to prevent migration of the simethicone from its volume portion of the tablet into the volume portion containing the antacid, and vice versa. The simethicone is physically combined with the other ingredients of the tablet in such a manner that the simethicone is available relatively immediately for antifoaming action, and its availability does not depend upon the breakdown of a matrix.

9 Claims, 4 Drawing Figures

SIMETHICONE ANTACID TABLET

BACKGROUND OF THE INVENTION

The present invention relates generally to pharmaceutical tablets and more particularly to a tablet containing both an antacid ingredient and an antigas ingredient consisting of simethicone.

Simethicone is described in the NATIONAL FORMULARY, 14th Edition, American Pharmaceutical Association, Washington, D.C., 1975, at page 648, as a mixture of not less than 93% and not more than 99% of dimethylpolysiloxane and not less than 4% and not more than 4.5% of silicon dioxide. Other characteristics of simethicone are described in the aforementioned publication at the page indicated, and that description is incorporated herein by reference. Dimethylpolysiloxane is sometimes referred to as polysiloxane or organopolysiloxane.

Rider U.S. Pat. No. 3,422,189 discloses a pharmaceutical tablet containing both an antacid ingredient and an anti-gas ingredient consisting of simethicone (called "Anti-foaming agent" therein), and the description of said Rider patent is incorporated herein by reference. As disclosed in the prior art, simethicone is an anti-foaming agent, and it also has the property of relieving flatulency symptoms in the digestive tract of humans.

Another prior art patent which discloses the combination of antacid and organopolysiloxane is Feinstone U.S. Pat. No. Re. 25,205.

When simethicone is combined in a tablet with essentially only a lactose filler, the tablet remains relatively fast-acting flatulency-relieving and anti-foaming characteristics even after the tablet has had a long shelf life. However, the simethicone is mixed with antacid ingredients, such as magnesium hydroxide or aluminum hydroxide or both, the rapidity with which the simethicone performs its anti-foaming function decreases as the shelf-life of the combination antacid—simethicone tablet increases. A reduction in the rapidity of the anti-foaming effect is indicative of a reduction in the rapidity of the antiflatulency effect.

Yen U.S. Pat. No. 3,501,571 disclosed the adverse effect on the rapidity of the anti-foaming function of polysiloxane when the latter is intimately mixed with antacid in a non-layered tablet. Yen ascribes this adverse effect to the fact that the polysiloxane is absorbed by the antacid particles so that little, if any, polysiloxane is available for anti-foaming action until the antacid matrix breaks down. In contrast, other substances, according to Yen, adsorb polysiloxane and retain it on the surface of the adsorbing particle where the availability of the polysiloxane for immediate anti-foaming action is not dependent upon the breakdown of the carrier particle. Such substances include lactose, mannitol, sorbitol, sucrose and dextrose.

To combat the slow acting anti-foaming action arising when simethicone is mixed with antacids, commercial embodiments of antacid-simethicone tablets have been prepared as a multi-layered tablet in which the antacid ingredients are in one layer and the simethicone is in another layer also containing lactose, the simethicone-containing layer being separate and discrete from the layer containing the antacid ingredients. Although the simethicone in such a multi-layered tablet has a faster acting anti-foaming effect after a given shelf life than does the simethicone in a tablet in which both the simethicone and the antacid ingredients are intimately mixed together, the problem of slowed anti-foaming action is still present. In other words, the simethicone in such a multi-layer tablet still has slower acting anti-foaming characteristics after a given shelf life than does a simethicone-lactose tablet containing no antacid ingredients whatsoever.

Other prior art attempts to deal with this problem include McVean U.S. Pat. No. 3,767,794 and Buehler U.S. Pat. No. 4,127,650 which teach suspending or entraining microscopic particles of simethicone within a matrix of either sorbitol (McVean) or glycerol and corn syrup (Buehler), then mixing with antacid and tableting. In this form, the simethicone is insulated from the antacid in the same tablet. The drawback to each of these attempts is that little, if any, simethicone is available for anti-foaming action until the matrix, be it sorbitol or glycerol-corn syrup, breaks down; and such a tablet is relatively slow acting compared to a tablet in which the availability of simethicone does not depend upon the breakdown of a matrix.

Moreover, because there is no digestion in the stomach, but only in the intestines, the breakdown of the matrix in the stomach would be by dissolution, only, a relatively slow process; and it would be impossible for the matrix to pass out of the stomach before breakdown was complete, thereby depriving the stomach of the anti-foaming action of the simethicone in the undissolved part of the matrix passing out of the stomach.

SUMMARY OF THE INVENTION

The problem of slowed anti-foaming action, a problem present in prior art commercial embodiments of antacid-simethicone tablets, has been overcome by a tablet prepared in accordance with the present invention. In such a tablet, each of the antacid and the simethicone occupy a separate, discrete volume portion of the tablet. In addition, the two volume portions are separated by a barrier, such as a membrane or diaphragm or film, which maintains the simethicone in one volume portion of the tablet out of contact with the antacid in the other volume portion, and prevents one or the other from migrating from its particular volume portion to the other volume portion.

Each of the two volume portions may constitute a separate layer of a two layer tablet, and the barrier may be a plastic film sandwiched between the two layers. In this embodiment the simethicone-containing layer consists essentially of simethicone and a filler of lactose or other simethicone-adsorbing material.

In another embodiment, the volume portion occupied by the simethicone can comprise an inner core and the volume portion constituting the antacid ingredient can constitute an outer layer encompassing the inner core. In this embodiment, the barrier is disposed between the inner core and the outer layer and encompasses the inner core, and the outer layer encompasses the barrier. The simethicone may be present as a mixture of simethicone and lactose or other simethicone-adsorbing material, in which case the inner core is surrounded by a plastic film enclosure. On the other hand, the simethicone may be unmixed in which case it will be in a relatively viscous, liquid state, and the barrier between the simethicone and the antacid ingredients, in this case, comprises a container for the liquid simethicone, such as a soft, chewable gelatin capsule shell.

In all embodiments of a tablet in accordance with the present invention the simethicone is physically combined with the other ingredients of the tablet in such a manner as to provide a relatively fast acting anti-foaming action. As used herein the phrase "fast acting anti-foaming action" means that the availability of the simethicone for anti-foaming action does not depend upon the breakdown of a matrix. This is because, in a tablet in accordance with the present invention, the simethicone is exterior of any matrix formed by any of the other ingredients in the tablet, i.e. the simethicone is not absorbed or entrained within such a matrix, nor does it become so during extended shelf life.

This is in contrast to prior art tablets in which simethicone is physically combined with the other ingredients in such a manner that the simethicone is absorbed or entrained within such a matrix (or becomes so during extending shelf life), so that the availability of the simethicone for anti-foaming action depends upon the breakdown of the matrix, be it a matrix material, such as an antacid, within which the simethicone is absorbed or a matrix material, such as sorbitol or glycerol-corn syrup, within which microscopic particles of simethicone are suspended or entrained. Tablets of the type described in the immediately preceding sentence provide a relatively slow acting anti-foaming action.

Other features and advantages are inherent in the structure claimed and disclosed or will become apparent to those skilled in the art from the following detailed description in conjunction with the accompanying diagramtic drawings.

DETAILED DESCRIPTION

Figure 1:
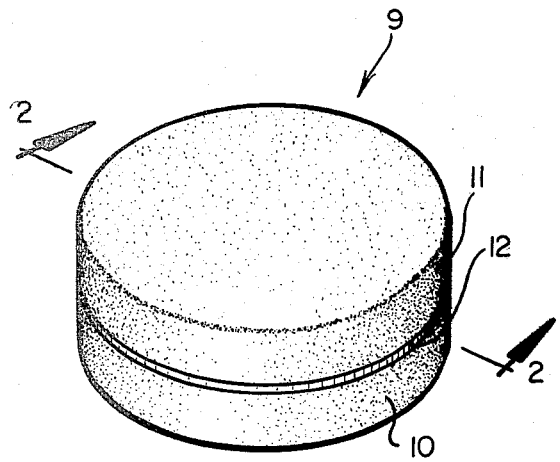
FIG. 1 is a perspective view of a pharmaceutical tablet in accordance with one embodiment of the present invention.
Figure 2:
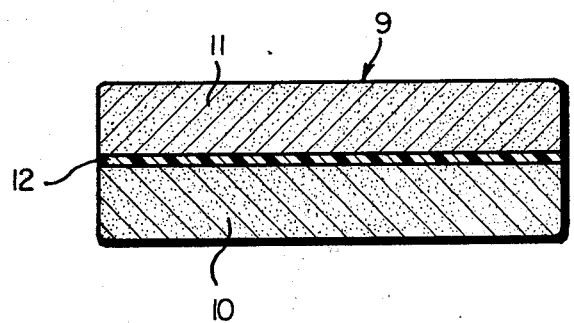
FIG. 2 is a sectional view of an embodiment of the present invention.

Referring to FIGS. 1 and 2, indicated generally at 9 is a tablet constructed in accordance with one of the embodiments of the invention. Tablet 9 comprises a first volume portion or layer 10 containing simethicone and a second volume portion or layer 11 containing antacid ingredients, with each of the first and second layers 10,11 being separate and discrete from the other layer. Sandwiched between layers 10 and 11 is a barrier 12 which may be a film or diaphragm or membrane composed of plastic material. Barrier 12 maintains the simethicone in first layer 10 out of contact with the antacid in second layer 11 and prevents migration of the simethicone from layer 10 to layer 11 as well as preventing migration of the antacid ingredients from layer 11 to layer 10.

Figure 3:
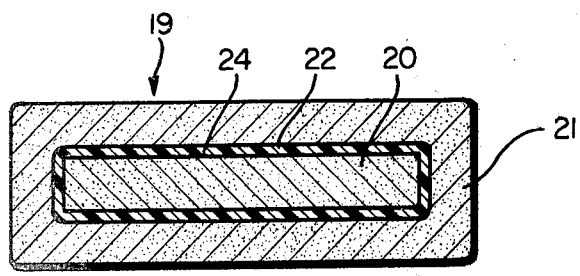
FIG. 3 is a sectional view of another embodiment of the present invention.

Referring to FIG. 3, in this embodiment 19, the first volume portion containing the simethicone is in the form of an inner core 20, and the second volume portion comprising the antacid ingredients is in the form of an outer layer 21 encompassing inner core 20. Barrier 22 is disposed between inner core 20 and outer layer 21 and encompasses inner core 20. Outer layer 21 encompasses barrier 22. Barrier 22 may be in the form of a thin plastic film or sheet surrounding and enclosing inner core 20, or barrier 22 may be in the form of a thin plastic film applied as a coating on the outer surface 24 of inner core 20 before outer layer 21 is formed.

In the embodiments of FIGS. 2 and 3, the volume portions 10 and 20, containing the simethicone, are each a mixture of ingredients comprising simethicone and a solid, inert filler or carrier of lactose or other simethicone adsorbing material.

Figure 4:
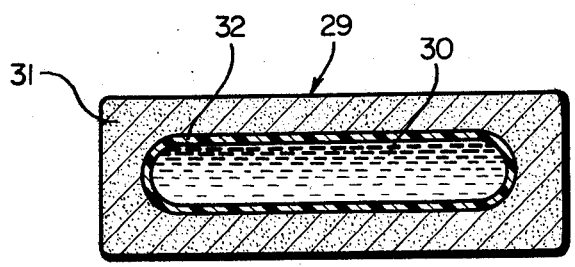
FIG. 4 is a sectional view of a third embodiment of the present invention.

Referring to FIG. 4, in this embodiment, 29 the first volume portion comprising the simethicone is in the form of an inner core 30 which may consist entirely of simethicone in its natural, viscous liquid condition. The outer core comprising the antacid ingredients 31 may be similar to the outer core 21 in the embodiment of FIG. 3. The inner core of simethicone is encompassed by and contained within a barrier 32 which may be in the form of a container for the liquid simethicone, e.g. a soft, chewable gelatin capsule shell. As an alternative to providing the simethicone within container 32 in its natural, viscous liquid condition, the simethicone may be provided as part of a solid mixture, as is the case with both the simethicone-containing layer 10 in the embodiment 9 of FIG. 2 and the simethicone-containing inner core 20 in the embodiment 10 of FIG. 3.

In all of the above-described embodiments, the simethicone is exterior of the matrix formed by the antacid in its respective volume portion (11,21 or 31), and the simethicone remains exterior of the antacid matrix during an extended shelf life because the barrier (12,22,32) prevents the simethicone from migrating into the acid and being absorbed by it. Similarly, in those embodiments in which the simethicone is part of a solid mixture with a simethicone adsorbing carrier material, such as lactose, the simethicone is exterior of the matrix formed by the carrier material because the simethicone is on the surface of the particles of carrier material, rather than being absorbed into the interior thereof. Thus, in all embodiments, the simethicone is available to perform its anti-foaming action without awaiting the breakdown of the matrix formed by either the antacid or the carrier material.

When the simethicone is part of a solid mixture, there are other suitable carriers or fillers for the simethicone, in addition to lactose. These include other sugars such as maltose, dextrose, fructose, sucrose, mannitol, sorbitol and the like, all of which are simethicone adsorbing materials. Other such materials are described in Yen U.S. Pat. No. 3,501,571 at column 2 and the description thereof is incorporated herein by reference.

The ingredients comprising the antacid layer of a tablet in accordance with the present invention are those antacid compositions heretofore conventionally utilized in antacid or antacid-simethicone tablets. Typical examples of such antacid ingredients are contained in the aforementioned patents of Rider U.S. Pat. No. 3,422,189, Yen U.S. Pat. No. 3,501,571, Feinstone U.S. Pat. No. Re. 25,205 and Buehler U.S. Pat. No. 4,127,650 and the disclosures in each of these patents relating to antacid ingredients is incorporated herein by reference. In a typical embodiment, the antacid ingredients will comprise magnesium hydroxide and aluminum hydroxide.

The material of which the barrier 12 or 22 is composed may comprise film-forming resins heretofore used in the formation of exterior coatings on pharmaceutical tablets. Examples of such resins are described in Endicott et al U.S. Pat. No. 2,881,085 which also describes combining these resins with hard, water soluble or water dispersible wax-like substances to enhance the ability of liquids in the digestive tract to penetrate through the film to the drug enclosed by the film-like coating. However, where the tablet is to be chewed (as is usually the case with tablets containing antacids) the water soluble or dispersible wax-like substances would appear to be dispensible. There are other ingredients which the aforementioned Endicott et al patent states may be combined with the film-forming resins, and these include water insoluble waxes, plasticizing agents and possibly wetting and drying agents.

Examples of film-forming resins which may be used as barrier material are the cellulose acetate pthalate resins including polycarboxycyclic acid partial esters of cellulose esters of lower aliphatic monocarboxycyclic acids, such as cellulose acetate phthalate, cellulose propionate phthalate and cellulose butyrate phthalate.

Specific examples of formulations containing such film-forming resins and their method of application are contained in the aforementioned Endicott et al patent, and the relevant portions thereof are incorporated herein by reference. These examples may be modified for use in accordance with the present invention by deleting the flavoring ingredients and those ingredients which are used to impart coloring or to improve the appearance of the coating or are otherwise specific to a coating which is on the exterior of a tablet, as distinguished from an internal barrier as in the present invention.

Additional barrier materials comprise (1) shellac dispersions, (2) hydroxethyl celluslose and sodium carboxymethylcellulose applied as alcoholic solutions, or (1) as a substrate with (2), (3) some natural and synthetic high melting point waxes and wax-like substances, and (4) polyvinylpyrrolidone alone or with acetylated monoglyceride.

Other materials may be utilized for the barrier between the two separate volume portions, the primary considerations being: (1) that the material is physiologically inert; (2) that it maintains each volume portion out of contact with the other; and (3) that it prevents migration of the simethicone from its volume portion to the volume portion containing the antacid ingredients and vice versa.

The soft, chewable, gelatin capsule comprising the barrier 32 in embodiment 29 of FIG. 4 can be a conventional gelatin capsule heretofore utilized in the pharmaceutical industry for chewable capsules.

Examples of tablets in accordance with the present invention and setting forth amounts of the various ingredients utilized are set forth below.

EXAMPLE I

First Volume Portion:
 Simethicone: 20 mgm.
 Carrier (lactose) 360 mgm.
Second Volume Portion:
 Aluminum Hydroxide: 200 mgm.
 Magnesium Hydroxide: 200 mgm.

EXAMPLE II

First Volume Portion:
 Simethicone: 80 mgm.
 Carrier: 935 mgm.
Second Volume Portion:
 Antacid: 800 mgm.

EXAMPLE III

First Volume Portion:
 Simethicone: 40 mgm.
 Carrier: 360 mgm.
Second Volume Portion:
 Antacid 400 mgm.

With respect to the filler or carrier of the foregoing examples, the filler may comprise lactose or other sugars, as described above, and, in addition, where appropriate, the carrier may also include conventional lubricants or binders heretofore utilized in the preparation of pharmaceutical tablets. Typical examples thereof are contained in the aforementioned Yen patent at column 3.

In a typical tablet in accordance with the present invention, the antacid ingredient will be present in the range 100–1000 mgms. and the simethicone will be present in the range 10–100 mgms. Preferably, the antacid is present in the range 300–800 mgms, and the simethicone is present in the range 20–40 mgms.

The tablets illustrated in FIGS. 2-4 may be prepared in accordance with conventional tableting procedures heretofore utilized for producing multi-layer tablets (FIG. 2) or tablets comprising an inner core of one ingredient surrounded by an outer layer containing another ingredient (FIGS. 3-4). The manufacturing procedure used in the preparation of such tablets is within the skill of the tableting art and does not constitute a part of the present invention.

Procedures for applying a film-like coating barrier 22 encompassing simethicone-containing layer 20 (FIG. 3) are determinable from descriptions in Endicott et al U.S. Pat. No. 2,881,085, and the descriptions therein are incorporated herein by reference. The film-like strip barrier 12 may be applied atop simethicone-containing layer 10 (FIG. 2) by spraying from above one or more times (at spaced intervals of time if spraying more than once) until a barrier of desired thickness (e.g. 0.005 in.) is obtained.

The foregoing detailed description has been given for clearness of understanding only, and no unnecessary limitations should be understood therefrom, as modifications will be obvious to those skilled in the art. For example, in the embodiment of FIG. 3, the inner core 20 may be antacid, and the outer layer 21 may contain the simethicone with the two discrete volume portions 20,21 separated by the same barrier 22 as is described above.

What is claimed is:

1. A tablet containing simethicone and an antacid, said tablet comprising:
 a first volume portions containing said simethicone;
 a second volume portion containing said antacid;
 each of said first and second volume portions being separate and discrete from the other volume portion;
 and barrier means between said first and second volume portions for maintaining the simethicone in said first volume portion out of contact with the antacid in the second volume portion and for preventing migration of ingredients from one volume portion to another;
 said simethicone being exterior of any matrix formed by any of the other ingredients in said tablet, the availability of the simethicone for anti-foaming action being independent of the breakdown of any such matrix.

2. A tablet as recited in claim 1 and comprising:
 two layers each constituting one of said first and second volume portions;

said barrier means being sandwiched between said two layers.

3. A tablet as recited in claim 2 wherein:
the layer constituting said first volume portion comprises simethicone and a solid carrier composed of simethicone adsorbing material.

4. A tablet as recited in claim 1 and comprising:
an inner core constituting said first volume portion;
and an outer layer constituting said second volume portion and encompassing said inner core;
said barrier means being disposed between said inner core and said outer layer and encompassing said inner core.

5. A tablet as recited in claim 4 wherein:
said inner core comprises simethicone and a solid carrier composed of simethicone adsorbing material.

6. A tablet as recited in claim 4 wherein:
said inner core comprises liquid simethicone;
and said barrier means comprises a container for said liquid simethicone.

7. A tablet as recited in claim 6 wherein:
said barrier means is a soft, chewable gelatin capsule shell.

8. A tablet as recited in claim 1 and comprising:
an inner core constituting said second volume portion and containing said antacid;
and an outer layer constituting said first volume portion and containing said simethicone;
said barrier means being disposed between said inner core and said outer layer and encompassing said inner core.

9. A tablet as recited in claim 8 wherein:
said outer layer comprises simethicone and a solid carrier composed of simethicone adsorbing material.

* * * * *

UNITED STATES PATENT AND TRADEMARK OFFICE
CERTIFICATE OF CORRECTION

PATENT NO. : 4,198,390

DATED : April 15, 1980

INVENTOR(S) : Joseph A. Rider

It is certified that error appears in the above–identified patent and that said Letters Patent are hereby corrected as shown below:

Col. 1, line 32, "remains" should be
--"retains"--

Col. 1, line 35, "the" should be
--"when"--

Col. 1, line 43, "disclosed" should be
--"discloses"--

Col. 2, line 25, "impossible" should be
--"possible"--

Col. 3, line 16, "extending" should be
--"extended"--

Col. 4, line 23, "10" should be
--"19"--

Col. 5, line 30, "celluslose" should be
--"cellulose"--

Col. 6, line 50, "portions" should be
--"portion"--

Signed and Sealed this

Twenty-ninth Day of July 1980

[SEAL]

Attest:

SIDNEY A. DIAMOND

Attesting Officer

Commissioner of Patents and Trademarks